United States Patent
Lagodzki et al.

(10) Patent No.: US 9,468,737 B2
(45) Date of Patent: Oct. 18, 2016

(54) PERFUSION REGULATION SYSTEM

(71) Applicant: Cook Medical Technologies LLC, Bloomington, IN (US)

(72) Inventors: Karol Lagodzki, Bloomington, IN (US); Trevor Plassman, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 35 days.

(21) Appl. No.: 14/326,978

(22) Filed: Jul. 9, 2014

(65) Prior Publication Data

US 2015/0018937 A1 Jan. 15, 2015

Related U.S. Application Data

(60) Provisional application No. 61/845,683, filed on Jul. 12, 2013.

(51) Int. Cl.
| | |
|---|---|
| *A61M 25/00* | (2006.01) |
| *A61M 25/10* | (2013.01) |
| *A61M 25/06* | (2006.01) |
| A61B 17/22 | (2006.01) |
| A61M 1/36 | (2006.01) |
| A61M 39/22 | (2006.01) |

(52) U.S. Cl.
CPC ..... *A61M 25/0021* (2013.01); *A61M 25/0662* (2013.01); *A61B 2017/22065* (2013.01); *A61B 2017/22067* (2013.01); *A61M 1/3613* (2014.02); *A61M 25/0026* (2013.01); *A61M 25/0097* (2013.01); *A61M 2025/0004* (2013.01); *A61M 2025/0042* (2013.01); *A61M 2025/0681* (2013.01); *A61M 2025/1052* (2013.01); *A61M 2025/1097* (2013.01); *A61M 2039/229* (2013.01)

(58) Field of Classification Search
CPC A61F 2/06; A61F 2002/068; A61M 1/3613; A61M 2025/0042; A61M 2025/1097; A61M 2039/2229; A61M 25/00; A61M 25/0021; A61M 25/10; A61M 39/22; A61M 25/104; A61M 1/36; A61M 2025/1052; A61M 25/0662; A61M 2025/0681; A61M 1/0084; A61M 1/3653; A61M 1/3659; A61B 17/12022; A61B 17/12027; A61B 17/12031; A61B 17/12036; A61B 17/12099; A61B 17/12109

See application file for complete search history.

(56) References Cited

U.S. PATENT DOCUMENTS

| | | | | |
|---|---|---|---|---|
| 4,592,754 A | * | 6/1986 | Gupte | A61F 2/064 604/9 |
| 5,106,363 A | | 4/1992 | Nobuyoshi | |
| 5,211,631 A | * | 5/1993 | Sheaff | A61M 5/44 604/103.05 |
| 5,328,471 A | * | 7/1994 | Slepian | A61L 24/0031 128/898 |
| 5,421,825 A | | 6/1995 | Farcot | |

(Continued)

*Primary Examiner* — Adam Marcetich
(74) *Attorney, Agent, or Firm* — Brinks Gilson & Lione

(57) ABSTRACT

A reperfusion system and method of perfusing a blood vessel using the reperfusion system are provided. The system includes an introducer sheath, a middle catheter extending through the introducer sheath, and a balloon microcatheter extending through the middle catheter. A connecting tube extends between a lumen of the introducer sheath and a valve at a proximal end of the microcatheter. A flow path is defined along a lumen of the introducer sheath, through the connecting tube, into the microcatheter, and out of a distal opening of the microcatheter. The balloon is disposed adjacent the exit point of the flow path to reduce reflux. Embolic material can be introduced into the microcatheter at the valve to exit at the same location as the blood flow.

4 Claims, 4 Drawing Sheets

(56) References Cited

U.S. PATENT DOCUMENTS

| | | | |
|---|---|---|---|
| 5,597,377 A | 1/1997 | Aldea | |
| 5,772,639 A * | 6/1998 | Lampropoulos | A61J 15/0042 604/264 |
| 5,833,650 A * | 11/1998 | Imran | A61M 25/1011 604/508 |
| 6,461,327 B1 * | 10/2002 | Addis | A61M 25/1011 604/101.04 |
| 6,569,148 B2 * | 5/2003 | Bagaoisan | A61B 17/22 604/101.04 |
| 6,622,367 B1 | 9/2003 | Bolduc et al. | |
| 6,726,651 B1 * | 4/2004 | Robinson | A61B 17/12045 604/101.01 |
| 8,057,497 B1 * | 11/2011 | Raju | A61B 17/22 604/22 |
| 2002/0151922 A1 * | 10/2002 | Hogendijk | A61B 17/12 606/192 |
| 2003/0050662 A1 * | 3/2003 | Don Michael | A61B 17/22 606/200 |
| 2004/0097995 A1 * | 5/2004 | Nash | A61B 17/32037 606/159 |
| 2005/0131453 A1 * | 6/2005 | Parodi | A61B 17/12 606/200 |
| 2006/0292206 A1 * | 12/2006 | Kim | A61B 17/12022 424/443 |
| 2010/0160863 A1 * | 6/2010 | Heuser | A61M 25/0662 604/164.1 |
| 2011/0301571 A1 | 12/2011 | Guimaraes | |
| 2012/0029436 A1 * | 2/2012 | Yassinzadeh | A61B 17/0057 604/187 |
| 2013/0317409 A1 * | 11/2013 | Cully | A61B 17/12036 604/6.09 |
| 2014/0018831 A1 * | 1/2014 | Kassab | A61B 17/12122 606/158 |

* cited by examiner

PERFUSION REGULATION SYSTEM

CROSS-REFERENCE TO RELATED APPLICATIONS

This application claims the benefit of U.S. Provisional Application No. 61/845,683, filed Jul. 12, 2013, which is hereby incorporated by reference in its entirety herein.

FIELD OF THE INVENTION

The present disclosure generally relates to medical devices. More specifically, the present disclosure relates to perfusion regulation systems.

BACKGROUND

In standard catheter embolization procedures, backflow may cause non-target embolization. This backflow may be caused by inadequate techniques employed by the person performing the treatment. Also, where pressure builds up distally such as with embolization procedures with microparticles and liquid embolic agents (glue/Onyx [Ev3]) backflow may result. This backflow may also result in non-target embolization. In order to prevent backflow, an occlusion balloon catheter may be used in the target vessel. However, inflation of the balloon stops the blood flow to the organs and or tissues of the target vessel which introduces additional risks.

SUMMARY

In overcoming the drawbacks and other limitations of the related art, the present disclosure provides artificial antegrade flow in the target vessel. The flow provides perfusion to the tissue and organs and is used to aid the embolic agent in reaching the target area. The present disclosure simultaneously combines no back flow when the balloon is insufflated, full embolization control, and enhanced safety.

The present invention includes an introducer sheath, a middle catheter extending through a lumen of the introducer sheath, and a balloon microcatheter extending through a lumen of the middle catheter. The microcatheter includes a valve at its proximal end having a first port and a second port, each of which are in fluid communication with the microcatheter lumen. A connecting tube extends between the second port and the introducer sheath lumen. Blood enters the introducer sheath lumen and travels through the connecting tube, into the microcatheter, and out of the distal end of the microcatheter. The first and second ports of the microcatheter valve each include a switch that can be opened and closed. Embolic material can be introduced into the microcatheter lumen through the first port. The middle catheter can include a middle catheter valve having a first port and a second port each in fluid communication with the middle catheter lumen. The microcatheter can extend through the first port. Contrast fluid can be introduced into the second port of the middle catheter valve and into the middle catheter lumen. The system can also include a supplemental tube extending between the connecting tube and the second port of the middle catheter valve so that blood can flow into the middle catheter lumen.

Further features and advantages of the present disclosure will become apparent from consideration of the following description and the appended claims when taken in connection with the accompanying drawings. It should be understood that the description and specific examples are intended for purposes of illustration only and are not intended to limit the scope of the present disclosure.

Figure 1:
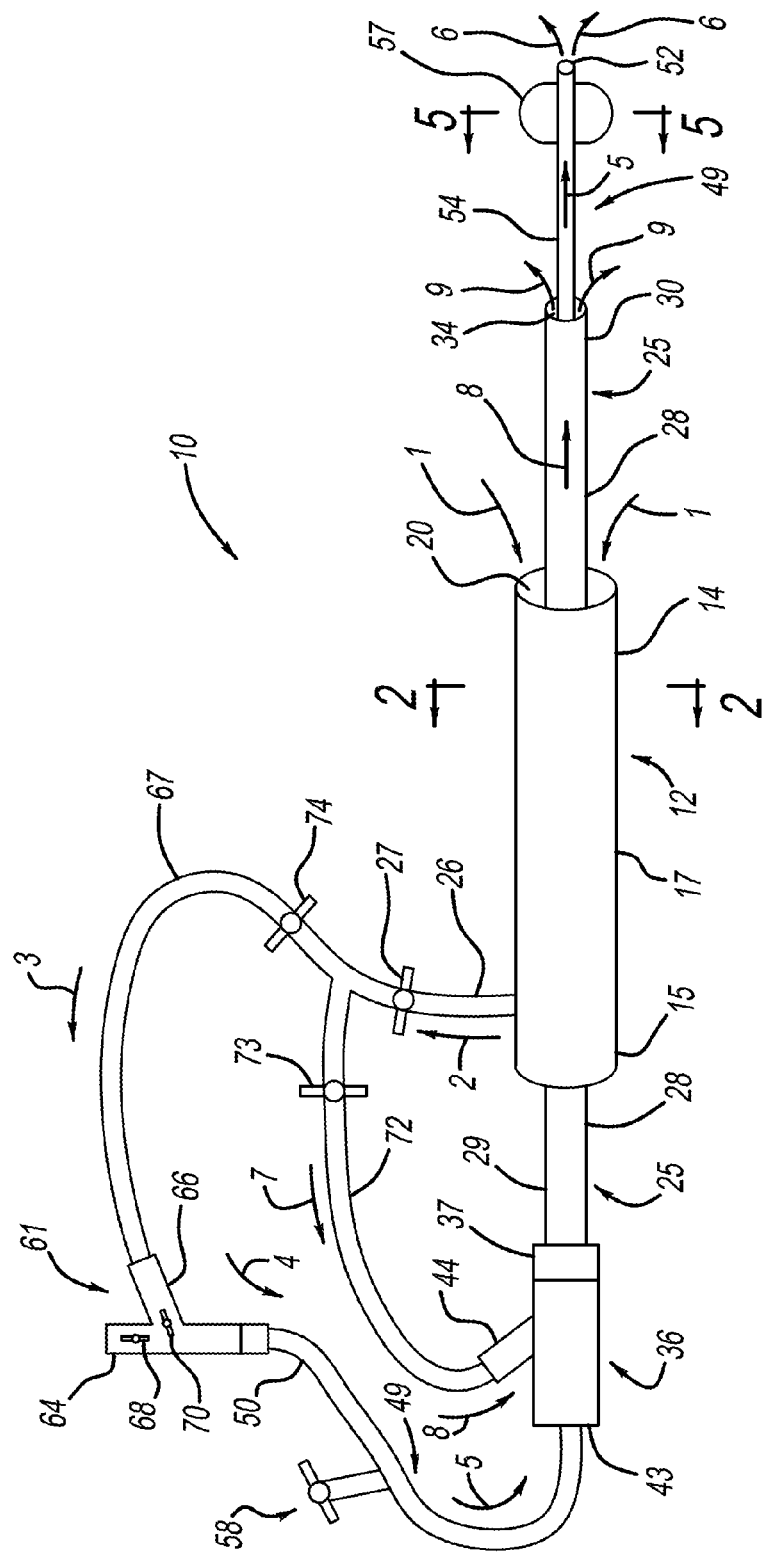
FIG. 1 is a side schematic view of a reperfusion system.
Figure 2:
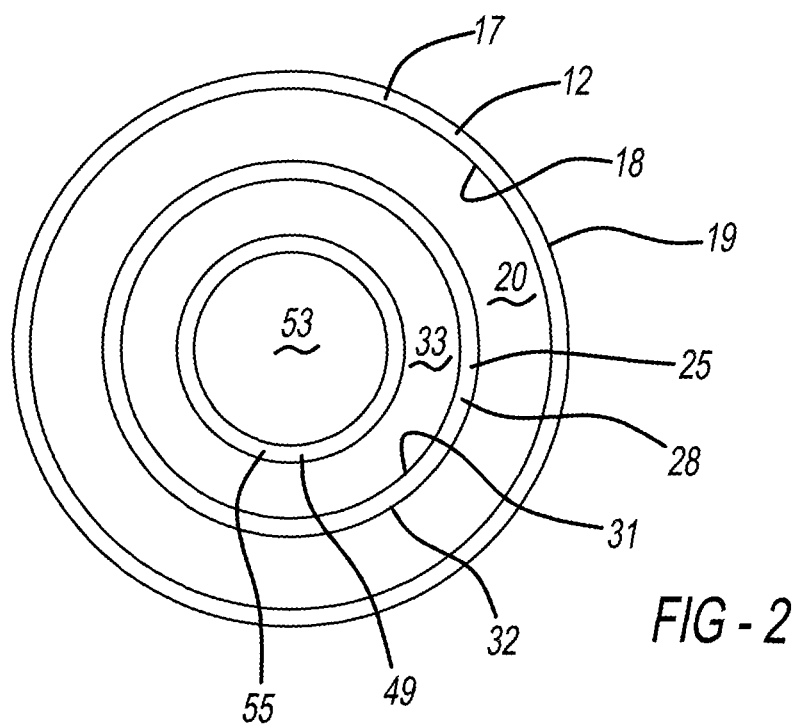
FIG. 2 is a cross-sectional view taken along lines 2-2 of FIG. 1.
Figure 3:
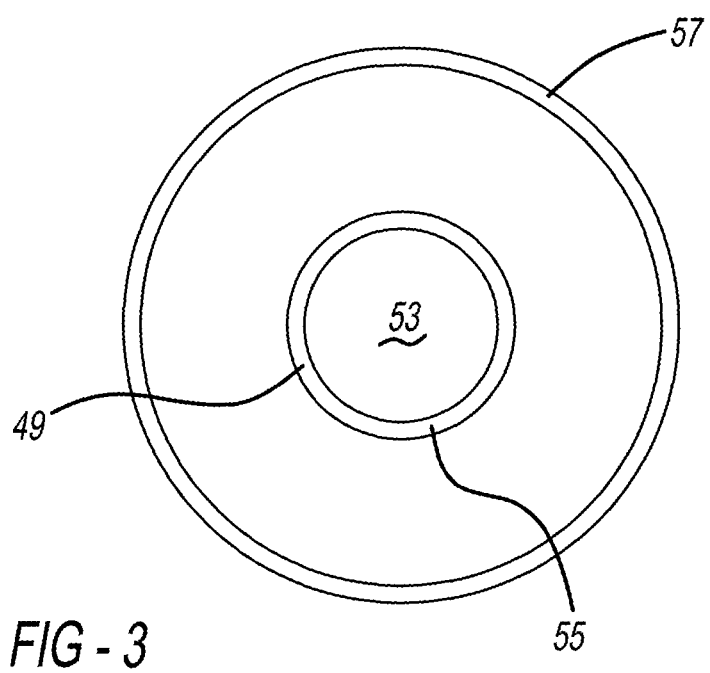
FIG. 3 is a cross-sectional view taken along lines 3-3 of FIG. 1.

The drawings described herein are for illustration purposes only and are not intended to limit the scope of the present disclosure in any way.

DETAILED DESCRIPTION

The present disclosure generally relates to a reperfusion system having an introducer sheath, a middle sheath within the introducer sheath, and a microcatheter within the middle sheath, where blood flow can enter the introducer sheath and be ultimately routed through the microcatheter to exit at its distal tip. The reperfusion system can be used in all types of embolization procedures including, but not limited to, chemo-embolization, radio-embolization, embolization of high flow blood vessels, situations where there is a high risk of non-target embolization, apparently safe situations in which a non-target embolization might lead to severe complications, and interventional oncology procedures where microparticles (a type of embolic agent) with chemotherapy or with radiation are injected into tumor vessels.

The term "substantially" used herein with reference to a shape includes variations in the recited shape that are equivalent to the shape for an intended purpose or function.

FIGS. 1-4 illustrate a reperfusion catheter system 10 which includes an introducer sheath 12 having a distal portion 14 and a proximal portion 15. A sheath wall 17 extends from the proximal portion 15 to the distal portion 14. The sheath wall 17 has an inner surface 18 and an outer surface 19. The inner surface 18 of the sheath wall 17 defines a longitudinal lumen 20 that extends to a distal end of the distal portion 14 to define a distal opening 20 of the introducer sheath 12.

The introducer sheath 12 may be made of polytetrafluoroethylene (PTFE), radiopaque fluorinated ethylene propylene (FEP), or combinations thereof, for example. The introducer sheath 12 may have any suitable size, for example about 7 French, about 8 French, or between about 7 French and about 8 French; however other sizes could also be used. The introducer sheath 12 has a thickness of about 0.020 inches, in a preferred form, but other suitable thicknesses can also be used. The introducer sheath 12 may be shorter in length than a typical introducer sheath in order to maximize the artificial antegrade blood flow as described in greater detail below. The introducer sheath 12 has the largest inner diameter possible in order to maximize antegrade blood flow intake around a middle catheter 25 (e.g. angiographic catheter) that is inserted through the lumen 20 in the introducer sheath 12. The outer diameter of the introducer sheath 12 is as small as possible in order to have a low profile and to minimize puncture site complications. The proximal portion 15 is attached to a lateral check flow 26 which includes a stopcock 27. The lateral check flow 26 is a side port that may be integrally formed with or attached to the introducer sheath 12 at the proximal portion 15.

The flexible middle catheter 25 has a catheter wall 28 that extends from a proximal portion 29 to a distal portion 30. The catheter wall 28 has an inner surface 31 and an outer surface 32. The catheter 25 defines a longitudinal lumen 33 that extends to a distal end of the distal portion 30 to define a distal opening 34 of the catheter 25.

The middle catheter 25, including the catheter wall 28, may be made of radiopaque vinyl (e.g. polyvinyl chloride), nylon, urethane, or combinations thereof, for example. The catheter 25 may have any suitable size, for example about 4 to 5 French, but other sizes can also be used in accordance with the selected size of the introducer sheath 12.

A detachable valve 36 (for example, a Touhy-Borst adapter) is attached to a hub 37 disposed at the proximal portion 29 of the middle catheter 25. The valve 36 has a first, main port 43 and a second, side port 44. The main port 43 will be described in further detail below. The side port 44 can be attached, in one embodiment, to an auxiliary supply source, such as a contrast fluid supply, to insert contrast fluid into the middle catheter 25 and out of the distal opening 34 of the middle catheter 25, which can help the user determine the location of various components of the system, which will be described in further detail below.

The system 10 also includes a balloon microcatheter 49 that has a proximal portion 50 and a distal portion 51, with a distal opening 52 at the distal end of the distal portion 51. The balloon microcatheter 49 is inserted through the lumen 33 in the middle catheter 25 to allow for antegrade blood-flow or embolization with microparticles, micro coils or liquid embolic agents (glue or Onyx [Ev3]). More specifically, the balloon microcatheter 49 is inserted into the middle catheter 25 through the main port 43 of the valve 36. The balloon microcatheter 49 includes an inner lumen 53 defined by a tubular wall 55 for delivering the antegrade blood flow or embolic agents.

The microcatheter 49, including its wall 55, may be made of PTFE, metal braids, nylon, PEBAX, or combinations thereof, for example. The microcatheter 49 may have any suitable size, for example about 2 French, about 2.8 French or between about 2 French and about 2.8 French. Of course, other sizes can also be used in accordance with the selected size of the introducer sheath 12 and the middle catheter 25. The outer diameter is preferably minimized. Also, the outer wall 55 of the microcatheter 49 is preferably made as thin as possible as long as there is no compromise in push ability and the ability to deliver the antegrade blood flow or embolic agents. Alternatively, embolic agents can be delivered through the middle catheter 25 without the use of the microcatheter 49, if desired. The catheter system 10 of the present invention is preferably comprised of polymers that provide the specific features of diameter compatibility, flexibility, torque-ability, and optimized blood flow.

An expandable member 57 (for example, an inflatable balloon) is attached at the distal portion 51 of the balloon microcatheter 49 just proximal from the distal opening 52. The balloon 57 may be made of polyurethane, nylon, or latex, for example. A side port 58 for providing inflation fluid to the balloon 57 intersects with the balloon microcatheter 49 at the proximal portion 50. The inner surface of the wall 55 defines an inflation lumen (not shown) that extends from the intersection of the side port 58 and the balloon microcatheter 49 to the inside of the balloon 57. The lumen 53 can be coaxially located inside the inflation lumen in a manner known in the art. A wall separates the inflation lumen and the lumen 53. In other embodiments, the inflation lumen may be located coaxially inside the lumen 53. In other embodiments, rather than being coaxial, the lumen 53 and the inflation lumen may be non-coaxially spaced away from each other inside the microcatheter 49. The balloon 57 can be expanded (e.g. inflated) by providing fluid through the side port 58 and through the inflation lumen in a manner known in the art.

In another form, the middle catheter 25 could include a second inflatable member (not shown) at its distal end similar to the inflatable member 57 disposed on the microcatheter 49. The middle catheter 25 would include the associated inflation lumen and side port for injecting inflation fluid in a manner known in the art.

The balloon microcatheter 49 includes a detachable valve 61 (such as a Touhy-Borst adapter), similar to the valve 36 of the middle catheter 25, disposed at the proximal portion 50. The valve 61 can be attached to a hub 62 of the microcatheter or attached in another manner known in the art. The valve 61 includes an outlet 63 in fluid communication with a first port 64 and a second port 66. The outlet 63 attaches to the microcatheter 49 so that the first and second ports 64, 66 are ultimately in fluid communication with the microcatheter lumen 53. The second port 66 is attached to a connecting tube 67 that extends to and is attached to the lateral check flow 26 of the introducer sheath 12.

Thus, the second port 66, connecting tube 67, and the lateral check flow 26 form a conduit or blood flow path that allows blood to flow from the introducer sheath 12 (which, for example, may be located in the lumen of the femoral artery) through the connecting tube 67 into the balloon microcatheter 49 and exiting through the distal opening 52 of the balloon microcatheter 49 at the target vessel location.

Figure 4:
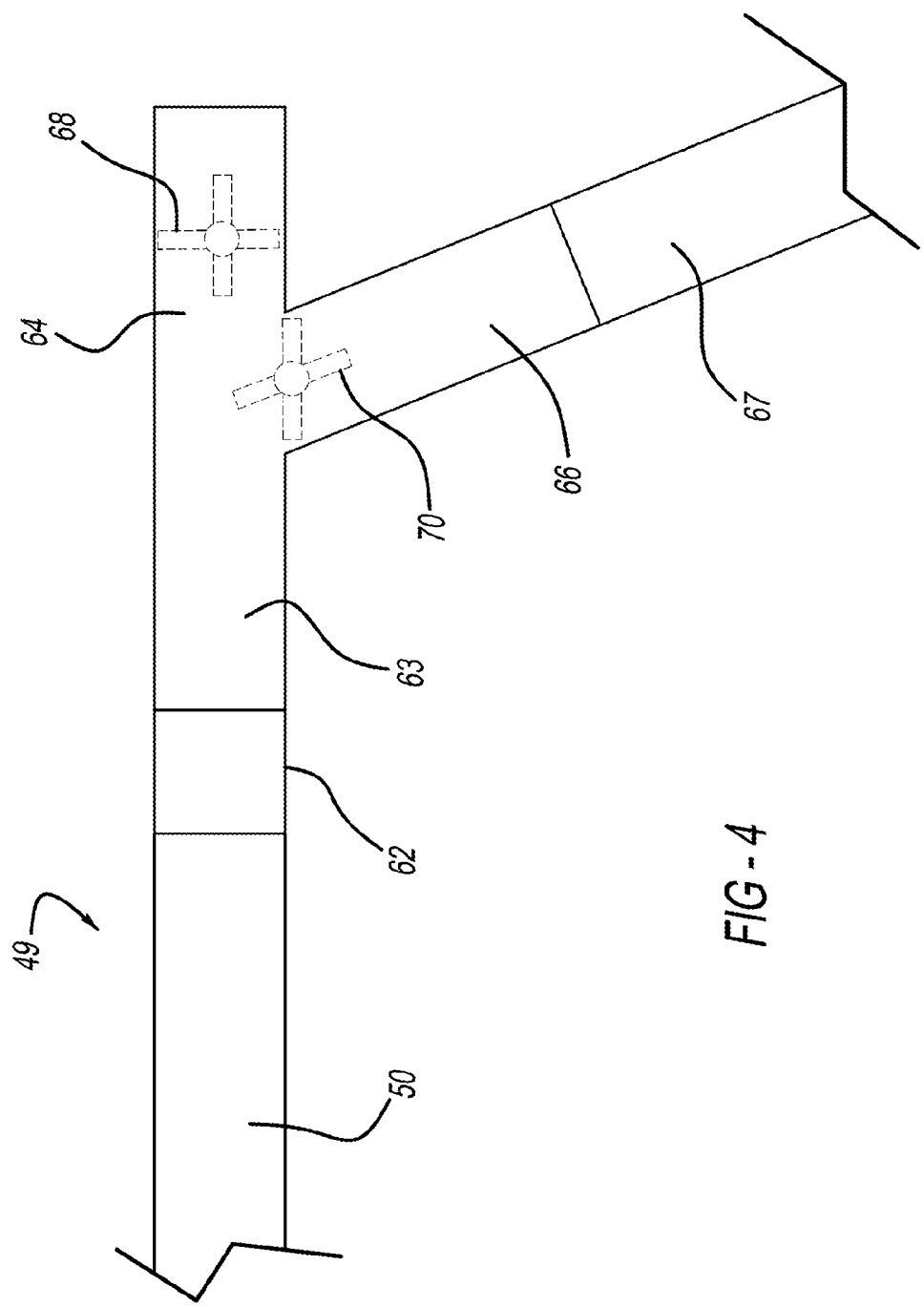
FIG. 4 is a schematic view of a valve of the reperfusion system.

The valve 61, shown in FIG. 1 and in further detail in FIG. 4, also includes a first valve switch 68 and a second valve switch 70. The switch 68 is moveable between a closed position and an open position for controlling introduction of embolic material or devices into the balloon microcatheter 49. The switch 70 is moveable between a closed position and an open position for controlling the antegrade blood flow through the conduit described above. More specifically, the switch 70 is disposed between the connecting tube 67 and the second port 66. The switches 68 and 70 are independently adjustable so that each can be open, each can be closed, or one can be open and one can be closed.

In one state, the switch 68 is closed and the switch 70 is open to allow for antegrade blood flow through the conduit while no embolic material is introduced through the first port. In another state, the switch 68 is open and the switch 70 is closed to allow for embolic material or devices to be introduced while antegrade blood flow is prevented from flowing through the microcatheter 49. In another state, both switches 68 and 70 are closed, where both flow and introduction of embolic material is prevented. In another state, both switches 68 and 70 are open to allow for simultaneous blood flow and introduction of embolic material. In one approach, the switch 68 is open to introduce embolic material and the switch 70 is closed to limit reflux during injection of the embolic material.

In another embodiment, a supplemental tube 72 intersects the tube 67 at a location between the lateral check flow 26 and the second valve 61. The supplemental tube 72 is in fluid communication with the tube 67 so that blood flow flowing through the conduit will also be directed into the supplemental tube 72. The supplemental tube 72 is connected to the side port 44 of the middle catheter valve 36 for directing blood flow into the lumen 33 of the middle catheter 25 so that blood will flow through the lumen 33 and around the microcatheter 49 when the microcatheter 49 is inserted. The supplemental tube 72 can include a second stopcock 73 along its length that is moveable between an open and closed position to allow for selecting whether blood will flow through the supplemental tube 72.

Similarly, the tube 67 can include a third stopcock 74 disposed between the intersection with the supplemental tube 72 and the second valve 61, which can be adjusted to allow for blood flow to the valve 61 or to block flow to the valve 61. Flow can be blocked to the valve 61, for example, if flow is desired through the supplemental tube 72 and the valve 36.

The selection of flow paths results in different exit points for the antegrade blood flow, which will be described in further detail below. If blood is flowing through the lumen 53 of the microcatheter 49, then blood will be directed to a location adjacent the distal opening 52 of the microcatheter 49. If blood is flowing through the lumen 33 of middle catheter 25, then blood will be directed to a location adjacent the distal opening 34 of the middle catheter 25. When the microcatheter 49 has been extended out of the middle catheter 25, then the distal opening 34 of the middle catheter 25 is located proximal to the distal opening 52 of the microcatheter 49. Thus, it will be appreciated that a user can select the desired flow path to select the location within the body vessel where blood will be reintroduced. Additionally, the user can select both paths so blood can be reintroduced at both locations, if desired.

Similarly, flow can be directed through the supplemental tube 72 and into the valve 36 so that it is directed to exit from the middle catheter 25 while embolic material is introduced at the valve 61 and directed to exit from the microcatheter 49. In this arrangement, the embolic material will be introduced at a location distal to the location where the blood is reintroduced. Of course, embolic material could also be introduced into the microcatheter 49 while blood flows through the microcatheter 49, either alternative to or in addition to blood flowing through the middle catheter 25.

While the introduction of embolic material has been described as being introduced at the valve 61, it is also possible to introduce embolic material at the first valve 36 so that it will enter the body vessel from the distal end of the middle catheter 25. This can be performed by introducing embolic material through the main port 43 of the valve 36 if the microcatheter 49 is not installed. Alternatively, this can be performed by introducing the embolic material through the side port 44 of the valve 36 with the microcatheter 49 installed, and the embolic material will flow through the middle catheter 25 and around the microcatheter 49.

As mentioned above, blood flow enters the system 10 at the distal end of the introducer sheath 12 and flows between the introducer sheath 12 and the middle catheter 25 toward the lateral check flow 26 and into the tube 67 for being directed through the system to exit at the distal end of the middle catheter 25 or microcatheter 49, or both. Entry of blood into the introducer sheath 12 can be provided in myriad ways. For example, FIGS. 5-8 illustrate introducer sheaths 13, 113, 213, 313, each having different patterns of openings 80, 180, 280, 380 on the sheath wall 17, and each of which can be used with the reperfusion system 10. A reperfusion system having similar introducer sheaths and openings is described in U.S. Patent Application No. 61/692,012, filed Aug. 22, 2012, which is hereby incorporated by reference in its entirety.

Figure 5:
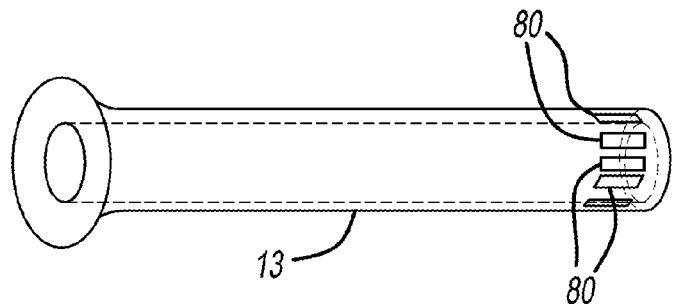
FIG. 5 is a side schematic view of an introducer sheath of the reperfusion system showing openings in the wall of the introducer sheath.
Figure 6:
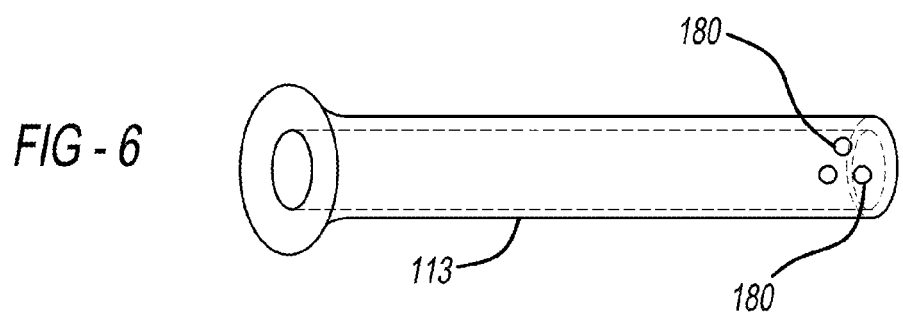
FIG. 6 is a side schematic view of another introducer sheath.

Each of the openings 80, 180, 280, 380 extend from the inner surface 18 to the outer surface 19 of the introducer sheaths 13, 113, 213, 313. The patterns and shapes of the openings may be designed to optimize blood flow into the introducer sheath 12, 113, 213, 313 and through the reperfusion system 10. FIG. 5 shows rectangular openings 80 which are circumferentially spaced apart around the entire circumference of the introducer sheath 12. FIG. 6 shows circular openings 180, two of which are longitudinally spaced apart on the introducer sheath 113. The circular openings 180 may also be circumferentially spaced apart the entire circumference of the introducer sheath 113. Additionally, as shown in FIGS. 5 and 6, the openings 80, 180 are formed only on the distal portion 18 of the introducer sheath 12, 113. In variations of the patterns of FIGS. 5 and 6, the openings 80, 180 may be spaced around only part of the circumference rather than the entire circumference.

Figure 7:
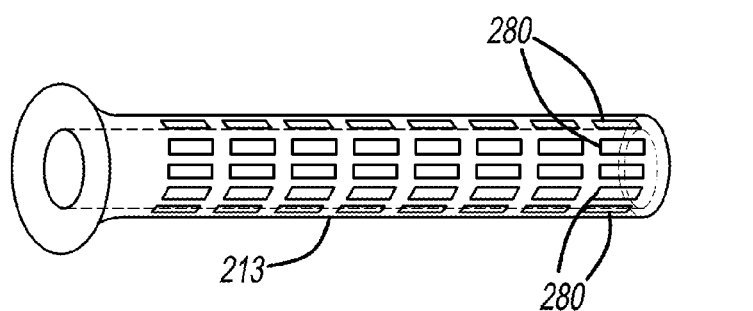
FIG. 7 is a side schematic view of another introducer sheath.
Figure 8:
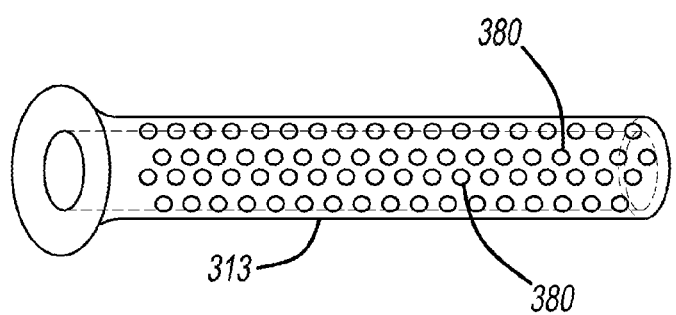
FIG. 8 is a side schematic view of another introducer sheath.

In variations of the introducer sheaths 13, 113, the introducer sheaths 213, 313, shown in FIGS. 7 and 8, show the openings 280, 380 spaced longitudinally along the entire length of the introducer sheaths 213, 313. Additionally, the openings 280, 380 may be circumferentially spaced apart around a part of or the entire circumference of the introducer sheaths 213, 313. In some embodiments, the openings 80, 180, 280, 380 may be located only on the proximal portion 15 of the sheaths 13, 113, 213, 313.

The shape of each opening may be a polygon or substantially a polygon, triangle or substantially a triangle, quadrilateral or substantially a quadrilateral, square or substantially a square, rectangle or substantially a rectangle, pentagon or substantially a pentagon, a hexagon or substantially a hexagon, an octagon or substantially an octagon, a circle or substantially a circle, an oval or substantially an oval, or an irregular shape. In some examples, a particular introducer sheath may openings of more than one shape, where the possible combinations may include any of the above shapes.

Alternatively, the system 10 can remain free of openings in the wall 17 of the introducer sheath 12 and blood flow can enter the system 10 through the distal opening of the sheath 12.

In operation the system 10 is used as follows. Once vascular access has been obtained (either arterial/venous), the introducer sheath 12 is introduced into body tissue, for example a blood vessel such as the femoral artery. In the lumen of the blood vessel (e.g. the femoral artery) where the introducer sheath 12 is introduced, the normal blood flow is in the direction of arrow A, for example if arterial entry of the introducer sheath 12 is done in the superior direction. Using standard catheterization techniques, the middle catheter 25 (e.g. angiographic catheter) is advanced selectively up to a target vessel. At the lumen of the target vessel, the normal blood flow is in the direction of arrow B. The blood flow may be in the direction of arrow B in both the vessel where the introducer sheath 12 is introduced, and in the target vessel, for example if arterial entry of the introducer sheath 12 is done in the inferior direction. In such examples, these entry vessel and target vessel may also, for example, be the same vessel.

The distance between the position where vascular access is obtained (e.g., the femoral artery) and the target vessel varies depending on the location of the target vessel. Accordingly, the length between the distal end 14 of the introducer sheath 12 and the middle catheter 25 will vary depending on how far the middle catheter 25 is extended into the vasculature.

In some examples, the middle catheter 25 is too large to advance into specific body tissue of a target vessel. In this case, the microcatheter 49 having the expandable member 57 can be advanced further and into the desired tissue and target vessel. For example, the middle catheter 25 can be used to access the Celiac trunk, and the microcatheter 49 can be used to access the target location for embolization that exists beyond the end of the middle catheter 25. The expandable member 57, being disposed just proximal from the distal end of the microcatheter 49, which is at the target embolization site, can therefore be disposed at the embolization site and to reduce reflux during embolization relative to an expandable member disposed proximal to the distal end of the middle catheter 25.

Once the microcatheter 49 and expandable member 57 are deployed to the target vessel, or before, the lateral check flow 26 of the introducer sheath 12 may be connected to the valve 61 by means of the connecting tube 67. An adapter such as, for example, a Luer-lock, can attach the valve 61 to the hub 62 of the microcatheter 49, or the valve 61 can be included in the microcatheter 49.

In the case where the supplemental tube 72 is included, the supplemental tube 72 can be attached to the tube 67 and connected to the first valve 36, which is connected to the middle catheter 25.

At this point, to stop the blood flow in the target vessel, the expandable member 57 (e.g. balloon 57) is expanded (e.g. insufflated, and thereby inflated) by providing fluid through the side port 58 and the inflation lumen of the microcatheter 49. The stopcock 27 can be switched from a closed position to an open position to allow blood from the common femoral artery to flow through the lateral check flow 26 and the valve 61 and through the microcatheter 49 into the target vessel. In the above scenario, the stopcock 73 located along the supplemental tube 72 is closed, or the supplemental tube 72 is not included in the system. Furthermore, the first switch 68 is closed and the second switch 70 is open so that flow through the tube 67 will pass through the valve 61 and into and through the microcatheter 49.

Of course, other flow paths and flow options can also be selected according to the description above. For example, the stopcock 74 of the tube 67 can be closed and the supplemental tube 72 can be used to direct flow so that the flow exits at the distal end of the middle catheter 25. In this approach, the middle catheter 25 preferably includes the second inflatable member and the balloon 57 of the microcatheter 49 remains deflated so that blood flow can ultimately reach the distal end of the microcatheter 49, which is where embolization is desired.

Similarly, adjustment of the various switches and stopcocks can be arranged to allow for blood flow through both the middle catheter 25 and the microcatheter 49.

To determine or confirm that the expandable member 57 has been properly inflated, a supply source of contrast fluid known in the art can be connected to the valve 36. In this approach, the supplemental tube 72 is disconnected or not included. Alternatively, the valve 36 could include a third port to connect the contrast fluid supply source while the supplemental tube 72 is connected. Contrast fluid is introduced and exits the distal end of the middle catheter 25 and will flow toward the inflated expandable member 57 located at the distal end of the microcatheter 49. The user can monitor the contrast fluid in a manner known in the art to determine whether or not the contrast fluid flows past the inflated balloon 57 to confirm or determine the inflation state of the balloon 57 and whether it has created a fluidic seal with the tissue at that location.

The above-identified technique provides an artificial/diverted antegrade flow towards the target vessel that is important to aid the embolic agent in reaching the target area distally, such as for treating a tumor in the microvasculature. Without having back blood flow in the target vessel when the balloon 57 of the microcatheter 49 is insufflated, there is a remarkable enhancement in procedure safety (antegrade flow, no back flow). By locating the balloon 57 at the distal end of the microcatheter 49 rather than the distal end of the middle catheter 25, reflux during embolization is further reduced. Moreover, by diverting blood flow through the microcatheter 49 in addition to or alternatively to the middle catheter 25, the rate and quantity of antegrade flow can also be improved relative to the flow only through the middle catheter 25.

The flow path for the blood is indicated by arrows numbered 1-6 in FIG. 1. As indicated by arrows 1, the blood flows into the distal opening and optionally through the wall openings 80 (if included) of the introducer sheath 12 and flows through the lumen 20 between the outer surface 32 of the middle catheter 25 and the inner surface 17 of the introducer sheath 12. The openings 29 are advantageous because they can improve flow into the introducer sheath 12, especially when there is little room for blood to flow into only the distal opening 20; however, sufficient flow can still be achieved without the inclusion of the openings 29. From the inside of the introducer sheath 12, the blood flows into the lateral check flow 26 to the stopcock 27 as indicated by arrow 2. The blood cannot flow through the introducer sheath 12 past the lateral check flow 26 because the proximal end is sealed. As indicated by arrow 3, after the blood exits the lateral check flow 26 it passes through the connecting tube 67 to the valve 61 of the microcatheter 49. The blood passes through the valve 61 into the microcatheter 49 as indicated by arrow 4. The blood then travels through the microcatheter 49 (e.g. through the lumen 53) as indicated by arrows 5 and exits at the distal opening 52 of the microcatheter 49 as indicated by arrows 6.

Flow through the supplemental tube 72 is indicated by arrow 7, where flow is diverted from the tube 67 and into the supplemental tube 72, which flows into valve 36 and through the middle catheter 25 as indicated by arrow 8. Flow will travel through the lumen 33 of the middle catheter 25 and around the microcatheter 49, and will exit from the distal opening 34 of the middle catheter 25 as indicated by arrows 9. As described above, this conduit can be used in addition to or as an alternative to the other flow path described in the preceding paragraph.

If contrast fluid is introduced, the fluid would enter at the valve 36 at arrow 8 and would follow the path indicated by arrows 8 and 9 in the same manner as the blood flow traveling along the same path.

Once the artificial antegrade blood vessel flow is established, embolization using standard techniques can be performed. More specifically, switch 68 is opened and embolic material is introduced into the valve 61, where the embolic material will travel through the conduit according to arrows 5 and 6, with the embolic material flowing through the lumen 53 of the microcatheter 49. In one approach, the switch 70 is closed so that blood is not flowing through the microcatheter 49 while embolic material is introduced. In another approach, both switches 68 and 70 are open so that both blood and embolic material flow through the same lumen together at the same time. Switch 68 can be closed to stop introducing embolic material.

In a high flow blood vessel, the balloon insufflation permits flow control. As there is no retrograde or backflow, there is full control to avoid non-target embolization that may potentially happen at any time during the current embolization techniques using the existing devices available in the market. The balloon 57 may be deflated at any time if needed, and the inherent/native antegrade blood vessel flow can be reestablished immediately.

The system 10 can include pumps or additional valves where syringes can be added to aspirate the various flow paths in order to increase flow throughout the system 10. The pump could be a manual pump or an automatic pump, depending on the needs of the user. The pump can be any suitable pump known in the art and used in a known manner.

As a person skilled in the art will readily appreciate, the above description is meant as an illustration of implementation of the principles of this invention. This description is not intended to limit the scope or application of this invention in that the invention is susceptible to modification, variation and change, without departing from the spirit of this invention, as defined in the following claims.

What is claimed is:

1. A method for controlling blood flow, the method comprising:
   delivering, to a body lumen, an introducer sheath having a wall defining a longitudinal lumen extending from a proximal portion to a distal end;
   advancing, through the lumen of the introducer sheath and out of the distal end thereof, a middle catheter having an outer wall and having a longitudinal lumen extending from a proximal portion to a distal end, wherein the middle catheter defines an outer surface that is free from an occluding device;
   advancing, through the lumen of the middle catheter and out of the distal end thereof, a microcatheter having a wall and having a longitudinal lumen extending from a proximal portion to a distal end, the microcatheter having an inflatable balloon on the distal end;
   receiving blood into the distal end of the introducer sheath;
   advancing the blood into a connecting tube having a first end in fluid communication with the inside of the introducer sheath and a second end in fluid communication with the microcatheter lumen;
   wherein the blood flows through a blood flow path defined between an inner surface of the introducer sheath and an outer surface of the middle catheter, through the connecting tube, through the proximal portion of the microcatheter, through the lumen of the microcatheter, and exiting the microcatheter distal end;
   wherein the middle catheter includes a middle catheter valve attached at the proximal portion thereof, the middle catheter valve includes a first port and second port each being in fluid communication with the middle catheter lumen, and the microcatheter extends through the first port into the middle catheter lumen; and
   wherein the flow path includes a supplemental tube connected to the second port of the middle catheter valve and extending therefrom to the flow path, wherein the flow path is in fluid communication with the second port of the middle catheter valve, the method further comprising advancing blood through the supplemental tube and into the second port of the middle catheter valve and into the middle catheter lumen.

2. The method of claim 1, wherein the microcatheter includes a valve comprising a first port with a first switch having open and closed positions and a second port with a second switch having open and closed positions, the first and second ports are in fluid communication with the microcatheter lumen, and the second port is in fluid communication with the connecting tube.

3. The method of claim 2 further comprising closing the first switch and opening the second switch to allow blood to flow through the flow path.

4. The method of claim 2 further comprising opening the first switch and closing the second switch to prevent blood from flowing through the flow path, and introducing embolic material into the microcatheter lumen via the first port.

* * * * *